(12) United States Patent
Turner et al.

(10) Patent No.: US 7,228,732 B2
(45) Date of Patent: Jun. 12, 2007

(54) TIRE WEAR ANALYSIS METHOD

(75) Inventors: John L. Turner, Akron, OH (US); David O. Stalnaker, Hartville, OH (US); James D. Ulmer, Akron, OH (US); Erik F. Knuth, Akron, OH (US)

(73) Assignee: Bridgestone Firestone North American Tire, LLC, Nashville, TN (US)

( * ) Notice: Subject to any disclaimer, the term of this patent is extended or adjusted under 35 U.S.C. 154(b) by 294 days.

(21) Appl. No.: 10/967,827

(22) Filed: Oct. 18, 2004

(65) Prior Publication Data

US 2005/0066719 A1 Mar. 31, 2005

Related U.S. Application Data

(63) Continuation-in-part of application No. 09/976,065, filed on Oct. 12, 2001, now Pat. No. 6,804,998, which is a continuation-in-part of application No. 09/770,884, filed on Jan. 26, 2001, now Pat. No. 6,532,811.

(51) Int. Cl.
*G01M 17/02* (2006.01)

(52) U.S. Cl. ............................................. 73/146; 73/8

(58) Field of Classification Search .................. 73/146, 73/146.2, 146.3, 146.4, 146.5, 146.8, 8
See application file for complete search history.

(56) References Cited

U.S. PATENT DOCUMENTS 3,563,088 A    2/1971    Sperberg
4,160,378 A    7/1979    Himmler
5,065,618 A    11/1991   Hodges, Sr. et al.
5,245,867 A    9/1993    Sube et al.
5,440,923 A    8/1995    Arnberg et al.
5,510,889 A    4/1996    Herr
5,557,552 A    9/1996    Naito et al.
5,561,244 A    10/1996   Olesky et al.
5,639,962 A    6/1997    Maloney (Continued)

FOREIGN PATENT DOCUMENTS

EP        0 880 019 A2    11/1998

(Continued)

OTHER PUBLICATIONS

Intl. Search Report Oct. 4, 2002.

(Continued)

*Primary Examiner*—Andre J. Allen
(74) *Attorney, Agent, or Firm*—Thomas R. Kingsbury; Fred Zollinger, III

(57) ABSTRACT

A method of developing a set of input forces used to analyze tire wear includes the steps of characterizing a wear course by driving a vehicle over the wear course and measuring data related to a plurality of forces experienced by the vehicle. A vehicle characterization model for a target vehicle having at least one tire is developed. The vehicle characterization model is used to calculate force data that represents the forces that would be experienced by at least one tire of the characterized vehicle if the characterized vehicle were driven over the characterized wear test course in the first vehicle configuration. The force data is then used to analyze tire wear using a computer prediction technique or by running an indoor wear test on the tire.

24 Claims, 3 Drawing Sheets

U.S. PATENT DOCUMENTS

| | | |
|---|---|---|
| 5,641,900 A | 6/1997 | Di Bernardo et al. |
| 5,657,227 A | 8/1997 | Freitag |
| 5,710,718 A | 1/1998 | Kamegawa et al. |
| 5,750,890 A | 5/1998 | Fricke et al. |
| 5,774,374 A | 6/1998 | Scott et al. |
| 5,877,414 A | 3/1999 | Rui et al. |
| 5,880,362 A | 3/1999 | Tang et al. |
| 5,900,542 A | 5/1999 | Fricke et al. |
| 6,083,268 A | 7/2000 | Kelsey et al. |
| 6,532,811 B2 * | 3/2003 | Turner et al. .................. 73/146 |
| 6,804,998 B2 * | 10/2004 | Turner et al. .................. 73/146 |
| 2002/0134148 A1 | 9/2002 | Turner et al. |
| 2002/0134149 A1 | 9/2002 | Shiraishi et al. |

FOREIGN PATENT DOCUMENTS

| | | |
|---|---|---|
| EP | 0 969 276 A2 | 1/2000 |
| EP | 0 955 534 B1 | 3/2000 |

OTHER PUBLICATIONS

A copy of a manuscript by Do. O. Stalnaker and J. L. Turner entitled Indoor Simulation of Tire Wear: Some Case Studies.

* cited by examiner

TIRE WEAR ANALYSIS METHOD

CROSS REFERENCE TO RELATED APPLICATION

This is a continuation-in-part application of 09/976,065 filed Oct. 12, 2001 claiming priority from U.S. Pat. No. 6,804,998 dated Oct. 19, 2004, which is a continuation-in-part application of 09/770,884 filed Jan. 26, 2001 now U.S. Pat. No. 6,532,811 dated Mar. 18, 2003; the disclosures of both are incorporated herein by reference.

BACKGROUND OF THE INVENTION

1. Technical Field

The present invention generally relates to methods of analyzing tire wear. More particularly, the invention relates to a method for determining a set of tire loads and using the set of tire loads to analyze tire wear.

2. Background Information

Automobile and tire manufacturers desire wear testing to be performed on tires. Different methods of wear testing tires are known in the art. In one known method, the test tires are placed on a vehicle that will be frequently driven. The tires are measured after the vehicle is driven a selected number of miles. Another known test procedure is performed indoor on a wear test drum. A wear test drum provides a rotating surface that engages the tire to simulate a road surface. The wear test drum provides mechanisms for varying the force between the tire and the rotating surface. The velocity of the rotating surface may also be varied. The user may simulate actual public road driving conditions by varying these forces and the velocity. The problem in the prior art is that the user cannot easily determine what forces and velocities to use to simulate public road driving conditions for a specific vehicle.

For instance, one may wish to simulate tire wear with a specific tire on a specific vehicle over a daily commute that includes country road, highway, and city road driving conditions. The total length of the daily commute over a one year period may be 15,000 miles. The forces between the tire and the road constantly change through this commute and the person conducting the indoor wear test desires to accurately simulate these forces on the test tire with the indoor test drum.

One method of predicting the tire forces is to instrument a test vehicle with wheel force transducers that are mounted as part of the wheel and rotate with the wheel/tire assembly while the vehicle is driven over a controlled test track. The vehicle is equipped with a data acquisition system that stores signals from the transducers. For instance, front and rear radial force, lateral force, drive/brake force, and tire velocities may be recorded. A problem with this measurement system is that the equipment is difficult to transport from test location to test location, the setup time is long, and the vehicle cannot be driven on public roads while equipped with the transducers. The data is thus only gathered on a test track that simulates public road driving conditions. The process of gathering the force histories for a given car with a given tire is expensive and often consumes weeks of time. The process must be repeated for different cars and for different tires. The art thus desires a faster and easier method of generating tire loading histories for indoor wear tests. The art also desires that the method for generating the tire loading histories result in more accurate load histories for the test machine.

Another problem faced by tire designers is that an automobile manufacturer desires information relating vehicle set up changes to tire performance including tire wear. This information may be desired before a vehicle is produced thus eliminating the possibility of measuring the tire performance on the actual vehicle.

SUMMARY OF THE INVENTION

One embodiment of the invention provides a method of developing a set of input forces used to analyze tire wear wherein the method includes the steps of: (a) characterizing a wear course by driving a vehicle over the wear course and measuring data related to a plurality of forces experienced by the vehicle; (b) creating a vehicle characterization model for a target vehicle having at least one tire wherein the tire wear is to be analyzed for the target vehicle; and (c) using the vehicle characterization model to calculate force data that represents the forces that would be experienced by at least one tire of the characterized vehicle if the characterized vehicle were driven over the characterized wear test course in the first vehicle configuration.

The invention also provides a method of predicting tire wear for a tire without running the tire on the vehicle wherein the includes the steps of: (a) characterizing a wear course by driving a vehicle over the wear course and measuring data related to a plurality of forces experienced by the vehicle; (b) characterizing a first vehicle configuration using a vehicle computer model to define a first vehicle characterization model; (c) using the first vehicle characterization model to calculate first force data that represents the forces that would be experienced by at least one tire of the characterized vehicle if the characterized vehicle were driven over the characterized wear test course in the first vehicle configuration; (d) using the first force data to create a first set of tire wear data; (e) characterizing a second vehicle configuration using the vehicle computer model to define a second vehicle characterization model; (f) using the second vehicle characterization model to calculate second force data that represents the forces that would be experienced by at least one tire of the characterized vehicle if the characterized vehicle were driven over the characterized wear test course in the second vehicle configuration; (g) using the second force data to create a second set of tire wear data; and (h) comparing the first and second sets of tire wear data to predict how the differences between the first and second vehicle configurations affect tire wear.

The invention further provides a method of analyzing tire wear for a vehicle wherein the method includes the steps of: (a) characterizing a wear course by driving a vehicle over the wear course and measuring data related to a plurality of forces experienced by the vehicle; (b) creating a vehicle characterization model for a vehicle for which the tire wear is to be analyzed; (c) using the vehicle characterization model to calculate force data that represents the forces that would be experienced by at least one tire of the characterized vehicle if the characterized vehicle were driven over the characterized wear test course; (d) using the force data with a first tire to create a first set of tire wear data; (e) using the force data with a second tire to create a second set of tire wear data; and (h) comparing the first and second sets of tire wear data to determine which of the first and second tires provides better tire wear performance for the characterized vehicle.

DETAILED DESCRIPTION OF THE DRAWINGS

The method of the present invention is generally performed by first characterizing the vehicle for which the tire is being wear tested. The method also requires a wear test course to be characterized. The invention combines a course characterization with a vehicle characterization to create a load history that is used to estimate tire wear by using a tire wear model or by using an indoor mechanical wear test machine to wear test the tire. The resulting wear estimate more accurately predicts the future wear characteristics of a tire because the input forces are generated from the actual forces experiences by a vehicle driven on a wear course. The uncontrolled effect of weather variability is also avoided. In addition to the convenience and accuracy advantages, the characterized test courses may be used with any vehicle characterization (including characterizations reflecting different vehicle set ups) to allow different vehicles (and different vehicle set ups) to be tested on a single course without the need to drive the vehicle over the course. The characterized test course may also be used to analyze a series of different tires on a single vehicle characterization to maximize the wear performance for the particular vehicle characterization. In addition, different courses may be used with a single vehicle characterization to compare how a tire will perform with a vehicle on different courses.

1. Vehicle Characterization.

The vehicle characterization step of this method measures the forces and inclination angles experienced by each tire of a vehicle under a variety of driving conditions. The vehicle characterization step is performed on the target vehicle for which the tires are to be wear tested. For instance, if the tire to be wear tested is going to be used on a specific passenger car, the specific passenger car (ideally) - or a similar car - should be used during the vehicle characterization step.

Figure 1:
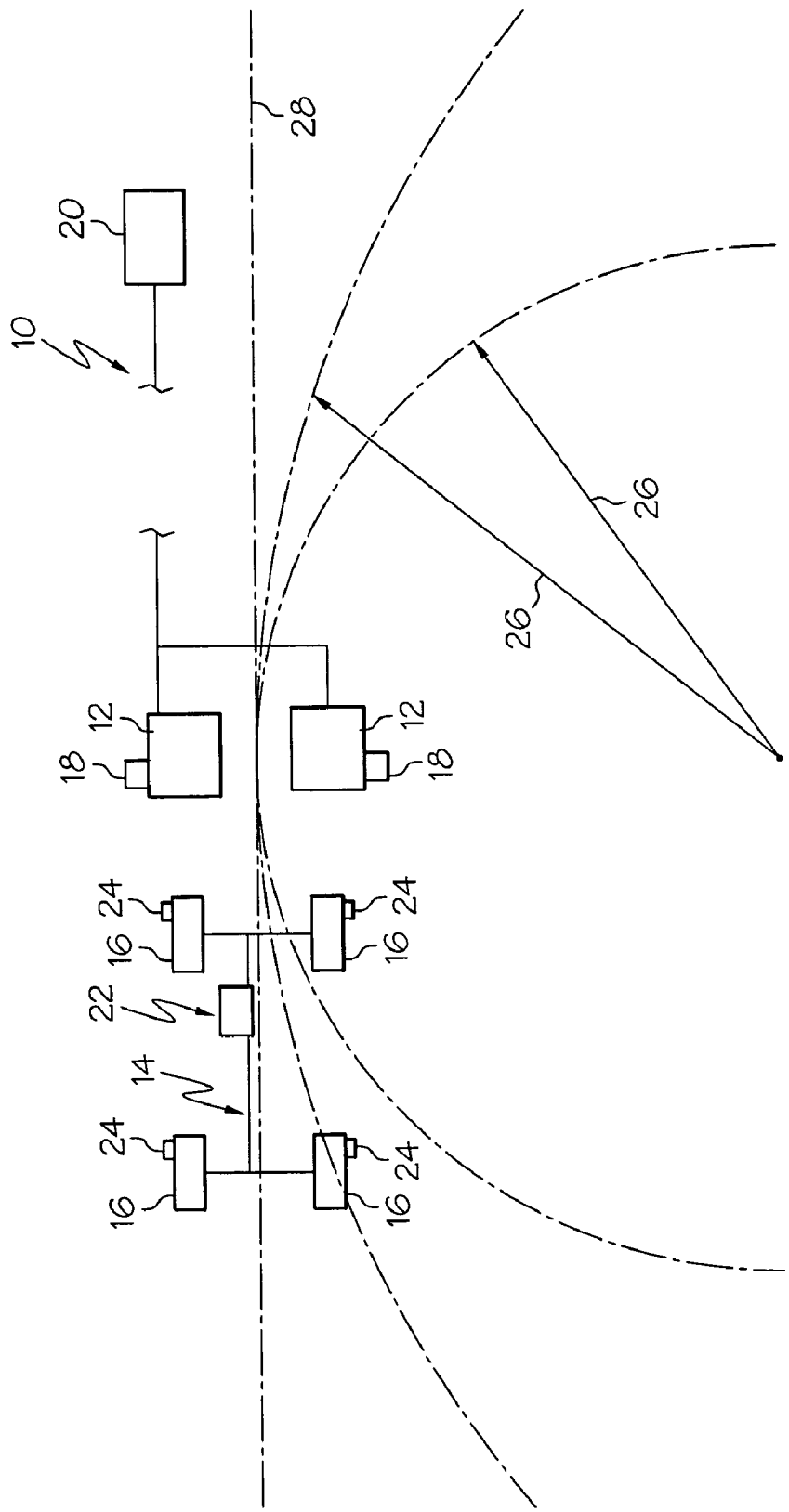
FIG. 1 is a schematic view of a dual force platform test facility.

The vehicle characterization step may be repeated for each type of vehicle for which a tire is to be wear tested. In one embodiment of the invention, the vehicle characterization data may be gathered using a dual force platform measurement system 10 (FIG. 1). One system known in the art is referred to as AMTI Model OR6-5-2000. This system includes in-ground force platforms 12 configured to be driven over by the vehicle 14. The platform spacing is adjustable to accommodate different vehicle track widths. When the tires 16 of the vehicle 14 engage the force platforms 12, three directional forces (fore-aft (Fx), lateral (Fy), and vertical (Fz)) are measured by transducers 18 and recorded by an appropriate storage device 20 such as a computer. The data may be immediately stored by computer 20 or stored in an intermediate storage device and then stored in computer 20. Transducers 18 may be in communication with storage device 20 by wires or wireless transmissions. A measurement device may be used to measure the speed of vehicle 14. In another embodiment of the invention, the vehicle speed may be processed from the data gathered as tires 16 pass over platforms 12.

In addition to the directional force measurements, transducers 22 are positioned at the vehicle center of gravity to measure accelerations (fore-aft, lateral, and vertical) during passage of tires 16 across force platforms 12. Appropriate wheel inclination measurement devices 24 are also used to measure the wheel inclination angles while tires 16 are passing over force platforms 12. One type of wheel inclination angle measurement device is disclosed in U.S. Pat. No. 5,561,244. Data from the two load platforms, the in-vehicle measurement of accelerations, and from the wheel inclination device are collected simultaneously.

The directional forces, velocity, accelerations, and wheel inclination angles are measured while vehicle 14 passes over platforms 12 at a range of speeds (for example, 2 to 20 miles per hour), turn radii 26 (for example, 30 feet to 200 feet), and straight driving acceleration/deceleration conditions 28 (for example, +0.5 g to −0.5 g). These test conditions span typically encountered levels of steering, cornering acceleration, braking acceleration, forward acceleration, and straight uniform motion produced in most day to day driving conditions on public roads and highways.

In another embodiment of the invention, the target vehicle is characterized with a computer model. For example, vehicle computer models are available from Mechanical Dynamics Corporation of Ann Arbor Michigan under the trademark ADAMS and from Mechanical Simulation Corp. under the trademark CarSim. The computer model allows a basic set of test maneuvers to be simulated for the vehicle. The basic maneuvers include city cornering, straight driving, lane changes, and acceleration/deceleration maneuvers. The maneuver simulations are run for the target vehicle- or a similar vehicle- and the accelerations, forces, and wheel inclination angles are recorded. The use of computer models for the vehicle characterization step allows the tire manufacturer to start a wear test before a vehicle is available. The computer models also allow different vehicle models to be created for a single target vehicle wherein the different vehicle models correspond to different vehicle set ups. For example, the different vehicle set ups may include changes to the alignment, toe angle, camber, and the like. The invention thus allows the user to determine how different vehicle set ups effect tire wear.

2. Course Characterization.

Figure 2:
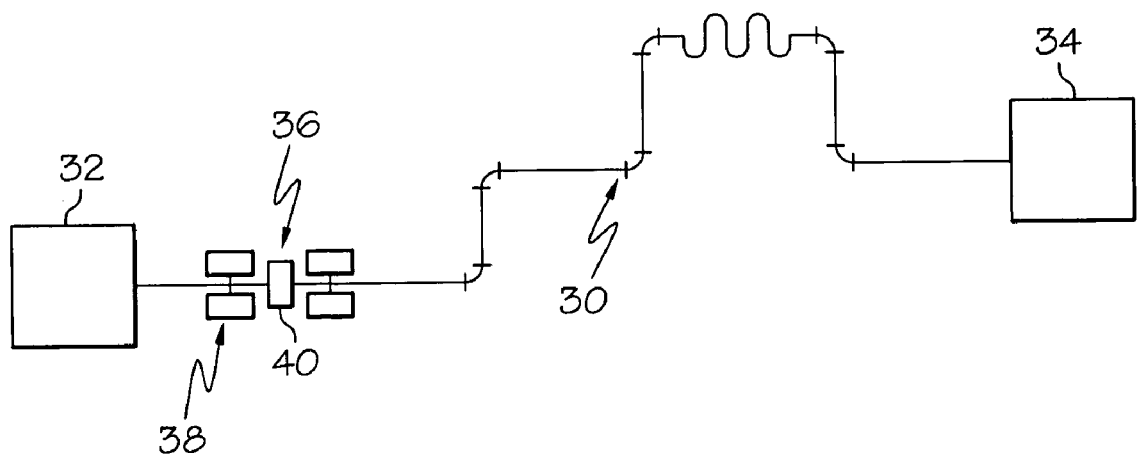
FIG. 2 is a schematic view of a wear test course being driven by a test vehicle.
Figure 3:
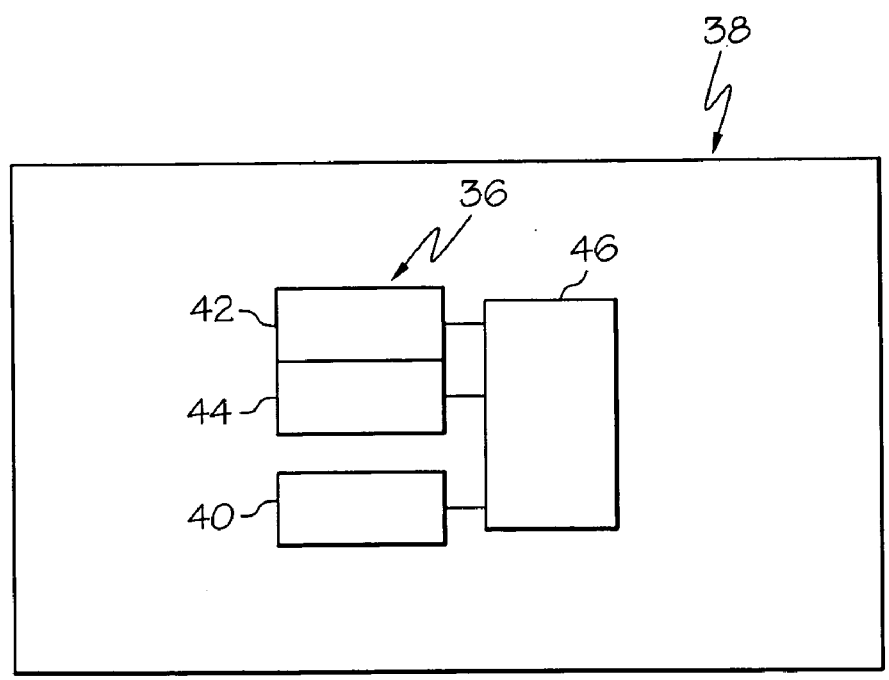
FIG. 3 is a schematic view of the instrumented vehicle depicted in FIG. 2.

Another step of the method of the present invention is to characterize a wear test course. A wear test course may be any test course of interest in which a tire manufacturer or automobile manufacturer is interested in gathering tire wear test information. For instance, the wear test course may be a typical commute for a target driver. In FIG. 2, a commuting wear course 30 includes a starting position at the driver's residence 32 and a final position at the driver's place of employment 34. The test course also may be a city driving course that would be typically used by a taxi cab driver. The wear test course may also be a route wherein the driver is given specific velocities for each part of the course. When the driver follows this type of course at the prescribed velocities, the accelerations experienced by the vehicle are relatively free of driver influence thus allowing this acceleration data to be used with a wide variety of vehicles regardless of the vehicle used to gather the data. A driver in a passenger car will not create significantly different data from the driver of a light truck because of the controlled velocities. The type of wear test courses available to the method of the present invention are essentially limitless.

Test course 30 is characterized by installing a measuring device 36 in a vehicle 38 that measures fore-aft, lateral, and vertical acceleration of the vehicle center of gravity while it is driven over course 30. An advantage is that test vehicle 38 does not have to be identical to test vehicle 14 described above. Another measurement device 40 records the velocity of the vehicle. Device 40 may be one that does not contact the road surface in order to determine velocity. Alternatively, device 40 measures the steering angle of vehicle 38 rather than the vehicle velocity. In one embodiment of the invention, three accelerometers 42, 43 and 44 are used to measure the fore-aft acceleration, the vertical acceleration, and the lateral acceleration. An appropriate data storage device 46 such as a personal computer may be in communication with measurement devices 40, 42, and 44 to record test data at regular intervals while vehicle 38 is driven over test course 30. In one embodiment, the data is recorded every one meter of travel over the entire wear test course 30. By gathering data based on distance instead of time, creating drive files is easier because the system does not gather data while the vehicle is stopped at a light or a stop sign. Gathering the data based on distance traveled is also logical because tire wear is primarily a function of distance traveled and not time. In one embodiment of the invention, a non-contacting, Doppler radar based velocity sensor (one example is available from Advanced Data Acquisition Corp.) is mounted under the vehicle close to the center of gravity. The sensor generates a signal proportional to the velocity and generates a signal that is used to pace data acquisition. This signal may be used to trigger data acquisition at a fixed distance (such as one meter) regardless of the velocity of the vehicle.

One advantage of this step over prior methods is that the instrumentation required to gather this data may be placed inside the vehicle allowing the vehicle to remain "street legal" and driven over public roads. In the past, the instrumentation was on the outside of the vehicle. The present invention also prevents inclement weather from ruining the data gathering steps. Another advantage is that devices 40, 42, and 44 are compact and may be easily shipped. The measurements devices may also be quickly installed in the test vehicle.

The data gathered over the wear test course 30 is stored and creates a mathematical test course that can be applied to different vehicles. Each cornering maneuver, each braking and acceleration event, every hill and town captured and reproduced, in real-time, in this mathematical test course. The user may drive multiple test courses in order to create a library of test courses that may be applied to vehicles as desired.

3. Model Development.

After the user has characterized a vehicle, the user develops equations (when not using a vehicle model as described above) that relate the fore-aft force (Fx), the lateral force (Fy), the vertical force (Fz), and the inclination angle (IA) to the fore-aft acceleration (Ax), lateral acceleration (Ay), vertical acceleration (Az) and velocity (Vx) (or steering angle), measured on the wear test course. The forces, inclination angle, and velocity are needed for the indoor wear test machine. The velocity is measured during the course characterization step discussed above. Thus, the equations must relate the forces and inclination angles to the data gathered during the course characterization step described above. The equations must also be able to be used to efficiently create the drive files necessary for programming the indoor wear machines.

The equations are of the following generic functional form:

$$\{Fz, Fy, Fx, IA\} = [K]\{1, Ay, Ay^2, Ax, Ax^2, Az, C, C^2, Vx^2\}$$

where $$K = \begin{matrix} K_{11} & K_{12} & K_{13} & K_{14} & K_{15} & K_{16} & K_{17} & K_{18} & K_{19} \\ K_{21} & K_{22} & K_{23} & K_{24} & K_{25} & K_{26} & K_{27} & K_{28} & K_{29} \\ K_{31} & K_{32} & K_{33} & K_{34} & K_{35} & K_{36} & K_{37} & K_{38} & K_{39} \\ K_{41} & K_{42} & K_{43} & K_{44} & K_{45} & K_{46} & K_{47} & K_{48} & K_{49} \end{matrix}$$

Figure 4:
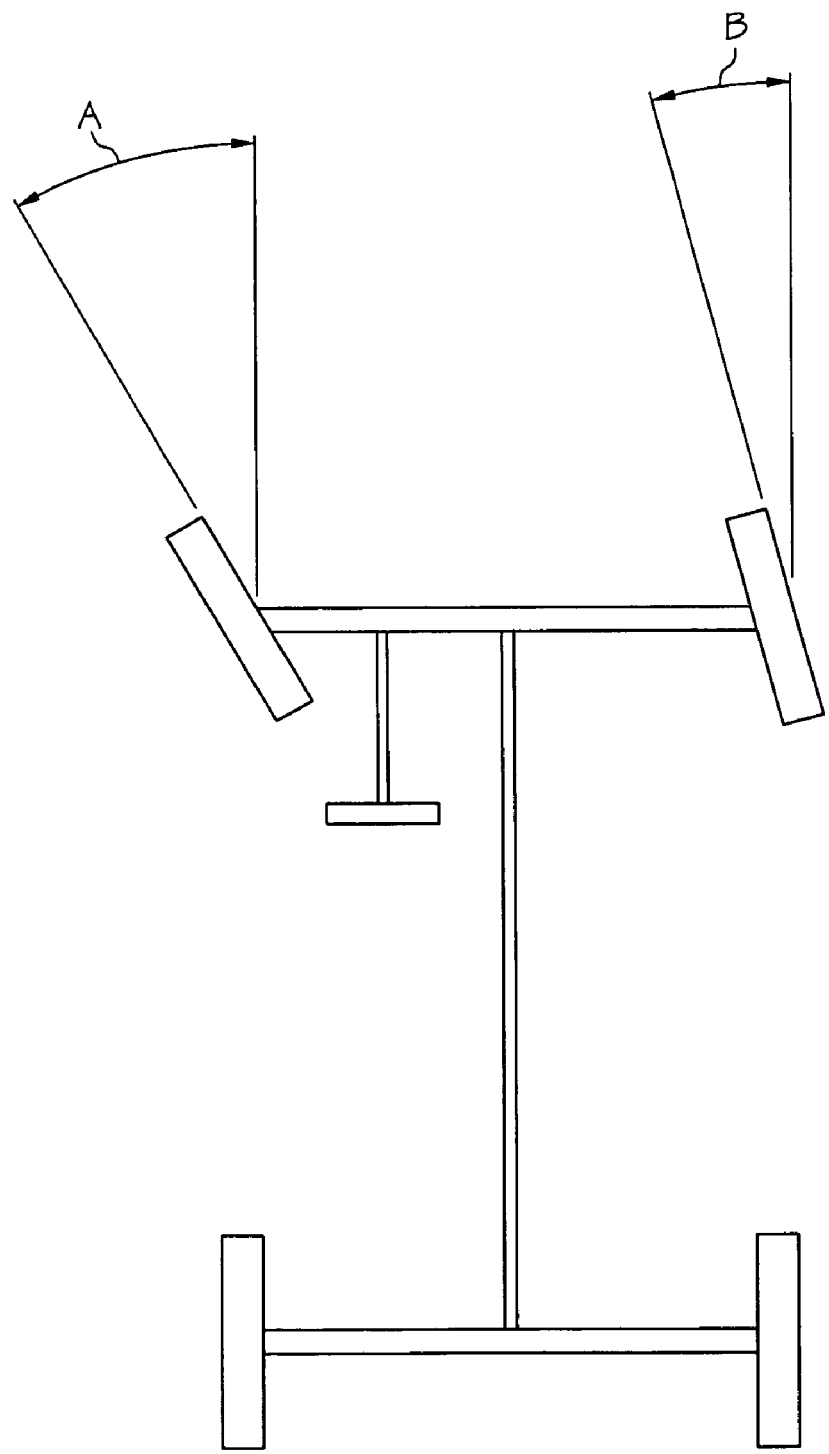
FIG. 4 is a schematic view of a vehicle showing the different steering angles of the front tires.

Fz, Fy, Fx, IA=Tire Loads and Inclination Angle
K=Vehicle Response Coefficients
1=Alignment Effects & Static Loads
Ay, $Ay^2$, Ax, $Ax^2$, Az=Inertial Contributions
C, $C^2$=Steering Kinematics
$Vx^2$=Aerodynamics These equations relate the forces and inclination angle to the vehicle accelerations, forward speed, and course curvature. A measure of the front position steer angle change is needed in the characterization step to account for the Ackerman effects that can significantly contribute to the lateral forces even in the absence of lateral accelerations. FIG. 4 shows why a vehicle steering system and vehicle geometry alters the angles of the tires with respect to the road surface. Angle A is different from angle B and thus the front tires experience different forces based on the radius of the curve. Road path curvature may be used to calculate these forces. However, road path curvature would have to be measured during the course characterization step. If it is not measured, the curvature may be calculated using the lateral acceleration and the velocity with the $C = A_y / V_x^2$ equation.

The coefficient matrix, K, defines the vehicle characteristics for wheel force and inclination angle dynamics. These equations are suitable for representing effects due to static loading, suspension characteristics, inertially induced load transfer, steering geometry effects, and aerodynamic contributions due to load transfer and inclination angle response. These equations have been developed for limited acceleration levels that generally do not exceed 0.5 g. This level is adequate for representing typical wear course and consumer driving conditions.

A separate set of matrix coefficients, K, are needed for each wheel position. In most situations, symmetry between left and right side wheel positions is an acceptable approximation. One method for computing the matrix coefficients uses a least squares regression to fit the modeling equations to the measured or computed-simulated data.

One additional modification is required if the indoor wear test machine (discussed in the next section) requires the spindle torque (My) as an input instead of Fx. In this case, an empirical, linear relationship between My and Fx is determined from a separate force and moment test machine for the tires under consideration and this relationship is used convert from Fx to My.

4. Indoor Mechanical Wear Test.

Once the equations relating the accelerations and velocities are known, the user may program an indoor mechanical wear test machine (such as the MTS Model 860 RoadWheel Tread Wear Test System) to simulate the outdoor wear test course. The user selects a characterized wear test course and calculates the forces as they relate to time for the vehicle. These forces are input into the indoor mechanical wear test machine and a number of miles is selected for the test. The indoor mechanical wear test machine rotates the tire against the drum and creates the forces input by the user. The wear test machine continuously repeats the wear test course as if the tire was being driven over the wear test course for the selected number of miles. For instance, the user may test the tire over a commuting course for 15,000 miles.

In another embodiment of the invention, tire wear may be predicted using an analysis technique such as finite element analysis. An exemplary computer model that uses finite element analysis is sold under the trademark Abaqus and may be used to perform tire wear estimates without running the tire on an indoor wear test machine. Other methods of estimating tire wear are disclosed in U.S. Pat. Nos. 5,710,718 and 6,083,268. Using the vehicle model with the wear course data explained below in combination with a methods to estimate tire wear allows the user to accurately analyze tire wear for a variety of different vehicle set ups or for a variety of tires with a single vehicle set up. The results allow the vehicle and tire designer to cooperate to provide a better tire and vehicle match that satisfies the desired vehicle set up while not overly sacrificing tire wear.

One exemplary use of the invention allows the user to analyze the effect of vehicle set up on tire wear. In this application, the user creates at least first and second vehicle models that represent first and second vehicle set ups. Both models are then used to calculate force data that represents the forces that would be experienced by at least one tire of the vehicle if the vehicle were driven over the wear test course. The two sets of force data are then used to predict or analyze tire wear—either by running a wear test machine or by using a technique to predict the tire wear. The user may then compare the tire wear results to determine how the vehicle set up change effected tire wear.

Another exemplary use of the invention allows the use to analyze how different tire configurations wear for a given vehicle set up. In this application, the user creates the vehicle model and calculates the forces data that represents the forces that would be experienced by at least one tire of the vehicle if the vehicle were driven over the wear test course. The user then uses the force data with a at least two different tires to create sets of tire wear data. The user may then compare the first and second sets of tire wear data to determine which of the first and second tires provides better tire wear performance for the characterized vehicle.

The method of the present invention allows tires to be efficiently and accurately wear tested using indoor testing equipment. The method allows the indoor testing equipment to effectively simulate each tire position of a particular vehicle traveling on a specific outdoor road wear course. The method allows the characterized vehicles to be tested on any characterized wear test course and allows a single wear test course to be used with any characterized vehicle.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A method of predicting tire wear for a tire without running the tire on the vehicle; the method comprising the steps of:
   (a) characterizing a wear course by driving a vehicle over the wear course and measuring data related to a plurality of forces experienced by the vehicle;
   (b) characterizing a first vehicle configuration using a vehicle computer model to define a first vehicle characterization model;
   (c) using the first vehicle characterization model to calculate first force data that represents the forces that would be experienced by at least one tire of the characterized vehicle if the characterized vehicle were driven over the characterized wear test course in the first vehicle configuration;
   (d) using the first force data to create a first set of tire wear data;
   (e) characterizing a second vehicle configuration using the vehicle computer model to define a second vehicle characterization model;
   (f) using the second vehicle characterization model to calculate second force data that represents the forces that would be experienced by at least one tire of the characterized vehicle if the characterized vehicle were driven over the characterized wear test course in the second vehicle configuration;
   (g) using the second force data to create a second set of tire wear data; and
   (h) comparing the first and second sets of tire wear data to predict how the differences between the first and second vehicle configurations affect tire wear.

2. The method of claim 1, wherein step (a) includes the step of measuring the fore-aft, lateral, and vertical accelerations experienced by the vehicle when the vehicle is driven over the wear course.

3. The method of claim 2, wherein step (a) further includes the step of measuring the velocity of the vehicle while the vehicle is driven over the wear course.

4. The method of claim 3, wherein step (a) includes the steps of mounting measuring devices to the vehicle and driving the vehicle over the wear course.

5. The method of claim 4, wherein the step of mounting measuring devices to the vehicle includes the step of mounting the measuring devices inside the vehicle.

6. The method of claim 2, wherein step (a) includes the step of measuring at fixed distances along the wear course.

7. The method of claim 2, wherein step (a) includes the step of driving the vehicle over a wear test course that includes public roads.

8. The method of claim 1, further comprising the step of inputting the force data into a tire model to predict the first and second sets of tire wear data.

9. The method of claim 1, further comprising the steps of inputting the force data into a wear test machine and performing indoor wear tests with the wear test machine using the force data to obtain the first and second sets of tire wear data.

10. A method of analyzing tire wear for a vehicle; the method comprising the steps of:
   (a) characterizing a wear course by driving a vehicle over the wear course and measuring data related to a plurality of forces experienced by the vehicle;
   (b) creating a vehicle characterization model for a vehicle for which the tire wear is to be analyzed;
   (c) using the vehicle characterization model to calculate force data that represents the forces that would be experienced by at least one tire of the characterized vehicle if the characterized vehicle were driven over the characterized wear test course;

(d) using the force data with a first tire to create a first set of tire wear data;

(e) using the force data with a second tire to create a second set of tire wear data; and (h) comparing the first and second sets of tire wear data to determine which of the first and second tires provides better tire wear performance for the characterized vehicle.

11. The method of claim 10, wherein step (a) includes the step of measuring the fore-aft, lateral, and vertical accelerations experienced by the vehicle when the vehicle is driven over the wear course.

12. The method of claim 11, wherein step (a) further includes the step of measuring the velocity of the vehicle while the vehicle is driven over the wear course.

13. The method of claim 12, wherein step (a) includes the steps of mounting measuring devices to the vehicle and driving the vehicle over the wear course.

14. The method of claim 13, wherein the step of mounting measuring devices to the vehicle includes the step of mounting the measuring devices inside the vehicle.

15. The method of claim 11, wherein step (a) includes the step of measuring at fixed distances along the wear course.

16. The method of claim 10, wherein step (a) includes the step of driving the vehicle over a wear test course that includes public roads.

17. The method of claim 10, further comprising the step of inputting the force data into tire models to predict the first and second sets of tire wear data.

18. The method of claim 10, further comprising the step of performing tests with an indoor wear test machine using the force data to obtain the first and second sets of tire wear data.

19. A method of developing a set of input forces used to analyze tire wear; the method comprising the steps of:

(a) characterizing a wear course by driving a first vehicle over the wear course and measuring data related to a plurality of forces experienced by the first vehicle;

(b) creating a vehicle characterization model for a target vehicle having a first vehicle configuration; the target vehicle having at least one tire wherein the tire wear is to be analyzed for the target vehicle; and (c) using the vehicle characterization model to calculate force data that represents the forces that would be experienced by at least one tire of the target vehicle if the target vehicle were driven over the characterized wear test course in the first vehicle configuration.

20. The method of claim 19, wherein step (a) includes the step of measuring the fore-aft and lateral accelerations experienced by the first vehicle when the first vehicle is driven over the wear course.

21. The method of claim 20, further comprising the step of mounting accelerometers to the first vehicle and driving the first vehicle over the wear course.

22. The method of claim 21, further comprising the step of mounting the accelerometers inside the vehicle.

23. The method of claim 20, wherein step (b) includes the steps of measuring three directional forces experienced by the tire on the vehicle; measuring the fore-aft and lateral accelerations the vehicle when the three directional forces experienced by the tire are measured; and creating formulas that relate the wear course accelerations to the three directional forces experienced by the tire.

24. The method of claim 19, wherein step (a) is performed with a first vehicle that is different than the target vehicle of step (b).

* * * * *